United States Patent [19]

Fukumoto et al.

[11] 4,101,795
[45] Jul. 18, 1978

[54] ULTRASONIC PROBE

[75] Inventors: Akira Fukumoto; Masami Kawabuchi; Hiroshi Fukukita; Jun-ichi Sato, all of Kawasaki, Japan

[73] Assignee: Matsushita Electric Industrial Company, Japan

[21] Appl. No.: 807,600

[22] Filed: Jun. 17, 1977

[30] Foreign Application Priority Data

Oct. 25, 1976 [JP] Japan .............................. 51 128472

[51] Int. Cl.$^2$ ............................................ H01L 41/10
[52] U.S. Cl. ................................ 310/336; 340/8 MM; 340/9; 128/2 V
[58] Field of Search ............... 310/334, 336, 337, 322; 340/8 MM, 9 R, 10, 15; 73/632, 628, 641; 128/2 V, 124 A

[56] References Cited

U.S. PATENT DOCUMENTS

| | | | |
|---|---|---|---|
| 2,408,028 | 9/1946 | Batchelder | 310/368 X |
| 3,166,731 | 1/1965 | Joy | 310/336 X |
| 3,971,962 | 7/1976 | Green | 310/335 X |

Primary Examiner—Mark O. Budd
Attorney, Agent, or Firm—Lowe, King, Price & Markva

[57] ABSTRACT

An ultrasonic probe particularly suitable for ultrasonic diagnostic equipments of the electronic scanning type is made up of a multiplicity of piezoelectric transducer elements, each in the shape of a rectangular plate with electrode films coated on both sides, arranged in a row at intervals and an acoustic impedance matching layer placed on the row of the transducer elements. The width-to-thickness ratio of each piezoelectric plate takes a value not greater than 0.8 and preferably between 0.4 and 0.7 so that the plate can vibrate in width expansion mode. It is highly preferable that the impedance matching layer has a laminated structure given by two layers which are different in acoustic impedance of the respective materials and individually have definite thicknesses.

12 Claims, 17 Drawing Figures

ULTRASONIC PROBE

This invention relates to an ultrasonic prove of the type utilizing piezoelectric transducer elements, which probe is particularly suitable for use in ultrasonic diagnostic equipments of the electronic scanning type.

Ultrasonic inspection in which either reflected or transmitted ultrasonic signal gives information on the interior of an object material is now of very wide application. The object of the inspection is not limited to metals and other various materials but includes human body: ultrasonic diagnostic equipments have proved of high appropriateness in various fields of clinics. Piezoelectric transducers are most widely used in current ultrasonic inspection or diagnostic equipments. When an electronic scanning technique is adopted in these equipments, a multiplicity of transducer elements are collected in a suitable arrangement into an ultrasonic probe which functions both as a transmitter and as a receiver.

The invention is concerned with vibration modes of the piezoelectric transducer elements in a multi-element ultrasonic probe. The construction and vibration modes of a conventional ultrasonic probe will firstly be outlined with reference to FIGS. 1–3 of the accompanying drawings.

Figure 1:
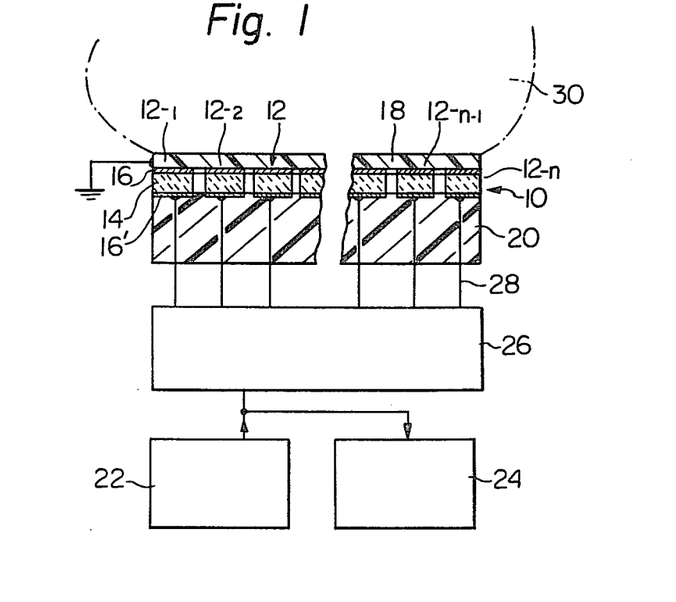
FIGS. 1–3 show the shape and arrangement of transducer elements in a conventional ultrasonic probe.
Figure 2:
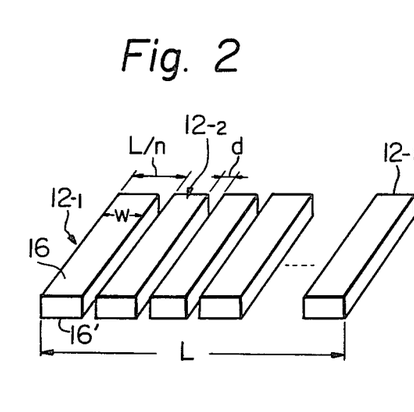

In FIG. 1, a conventional ultrasonic probe 10 for an inspection equipment of the electronic scanning type has a multiplicity of ($n$ pieces) transducer elements 12 (12-1, 12-2, . . . , 12-$n$), each consisting of a rectangular plate 14 of a piezoelectric substance, which may either be a crystalline material such as quartz crystal or a ceramic material typified by lead zirconate titanate, and two thin electrode layers 16 and 16' respectively coated on the front and back surfaces of the piezoelectric plate 14. The electrode layers 16, 16' are formed by plating, vacuum evaporation or application of a conductive paint. As shown in FIG. 2, the transducer elements 12 are usually arranged straight in a linear row at equal intervals $d$ with their longer sides opposite to each other. Sometimes, however, either a one-dimensional nonlinear arrangement or a two-dimensional arrangement of the elements 12 is employed instead of the illustrated one-dimensional linear arrangement. The probe 10 usually has an acoustic impedance matching layer 18 which takes the form of a plate placed on the row of the elements 12 so as to intimately cover the outer surfaces of the front electrodes 16 of all the elements 12. An example of the material of the impedance matching layer 18 is a hardened epoxy resin containing tungsten powder dispersed therein. The probe includes a backing load layer 20 which is in intimate contact with the outer surfaces of the back side electrode layers 16' of all the elements 12, so that the row of the elements 12 is firmly sandwiched between the impedance matching layer 18 and the backing load layer 20. The above described epoxy-tungsten mixture may be utilized also as the material of the backing load layer 20, but the material may alternatively be selected from various metals, ceramics and synthetic resins.

In an ultrasonic inspection equipment, the probe 10 is electrically connected to a driving circuit 22 for the excitation of the piezoelectric transducer elements 12 and a receiving circuit 24 for treating a reflected signal received by the transducer elements 12 (the treated signal is transmitted to a display instrument or a recorder) with the interposal of an electronic switching circuit 26 for scanning. Reference numeral 28 indicates lead wires connecting the transducer elements 12 with the switching circuit 26. In operation, the outer surface of the acoustic impedance matching layer 18 is brought into contact with an object 30 of inspection, for example human body in the case of ultrasonic diagnostic equipment.

Figure 3:
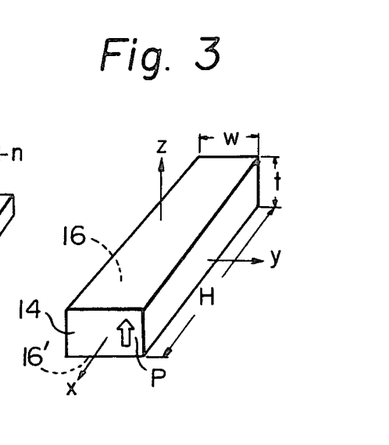

The vibrational characteristic of the piezoelectric plates 14 is a principal factor in the function of the ultrasonic probe 10. All the plates 14 have the same hexahedral shape, usually the shape of a comparatively elongate and thin rectangular plates as seen in FIGS. 2 and 3. The longitudinal, latitudinal and vertical axes of each plate 14 will be designated respectively as $x$, $y$ and $z$ (as indicated in FIG. 3), and the length H, width W and thickness $t$ of the plate 14 are defined respectively as the dimensions along the $x$, $y$ and $z$ axes. When the plate 14 is of a piezoelectric crystalline material, the $c$-axis of the crystal is usually made to be the $z$-axis of the plate 14. When the plate 14 is of a piezoelectric ceramic material, the material is polarized usually such that the direction P of the poralization coincides with the direction $z$ of the thickness of the plate 14. The electrode layers 16, 16' are formed on the surfaces parallel to the $x$-$y$ plane.

This transducer element 12 is designed with the intention of utilizing the piezoelectric plate 14 in a thickness longitudinal vibration mode, and it is a common practice to cause half-wavelength resonance in the direction $z$ of the thickness of the plate 14. Then the thickness $t$ of the piezoelectric plate 14 is determined by Equation (1):

$$t = \frac{\Lambda}{2} = \frac{1}{2} \cdot \frac{V}{f} \qquad (1)$$

where $\Lambda$ is the wavelength, V is the velocity of the ultrasonic wave in the piezoelectric plate 14, and $f$ is the frequency.

When $n$ pieces of the elements 14 are arranged at equal intervals $d$ in a linear row to give an entire length L (which may be regarded as an effective width of the probe 10) as shown in FIG. 2, the width W of each element 14 or plate 12 is naturally given by Equation (2):

$$W = \frac{L}{n} - d \qquad (2)$$

So far as we know, no particular attention has hitherto been given to the width W of the plate 14 aside from considerations of the relation between the number $n$ of the elements 12 in a probe 10 and the total width of the probe 10. The width-to-thickness ratio W/$t$ for the plate 14 is considerably great, usually greater than 10/1, in conventional ultrasonic probes for equipments which are provided with no electronic scanning circuit. When an electronic scanning technique is employed, there is a general trend of increasing the number $n$ of the elements 12 so that the ratio W/$t$ generally becomes small, for example about 3/1 or even smaller.

Primary vibration modes of the rectangular element 12 of FIG. 3 are thickness longitudinal vibration mode in which resonance occurs for a sound wave propagating in the direction $z$ and two kinds of width longitudinal vibration modes wherein resonance occurs respectively for sound waves propagating in the $x$- and $y$-directions. In the case of electronic scanning type equipments, the width W of the plate 14 is pretty close to the thickness t and sufficiently small relative to the length H, so that the width longitudinal vibration in the x-direction can be disregarded. It suffices to consider the thickness longitudinal vibration in the z-direction (will be abbreviated to TL vibration) and the width longitudinal vibration in the y-direction (abbreviated to WL vibration) as resonance modes.

We have recognized that an indiscrete shortening of the width W of the element 12 so as to become less than about five times the thickness $t$ causes interference of WL vibration modes with TL vibration and results in a considerable distortion of the ultrasound radiation pattern of the transducer element 12. When an ultrasonic inspection is performed using transducer elements which exhibit a distorted ultrasound radiation pattern, a visual information obtained by the test will inevitably show a deterioration in quality.

It is an object of the present invention to solve the above described problem encountered by conventional ultrasonic probes of the piezoelectric type.

It is another object of the invention to provide an improved ultrasonic probe of the piezoelectric type, the transducer elements of which probe can make an almost ideal piston vibration in their fundamental vibration mode without coupling with unwanted vibration modes.

It is a still another object of the invention to provide an improved ultrasonic probe of the described type, in which transducer elements of a rectangular plate shape are made to have a specific width-to-thickness ratio so as to make an almost ideal piston vibration.

It is a further object of the invention to provide an improved ultrasonic probe which is particularly suitable for ultrasonic diagnostic equipments having electronic scanning means.

An ultrasonic probe according to the invention comprises a plurality of transducer elements, each consisting of a rectangular plate of a piezoelectric material having a width-to-thickness ratio of not greater than 0.8 and two electrode films coated respectively on the front and back surfaces of the plate, and an acoustic impedance matching layer. The transducer elements are arranged in a row at intervals with their longer sides opposite to each other. The acoustic impedance matching layer has a laminated structure consisting of a uniformly thick inner layer of a first material of which acoustic impedance is 2.5 to 9.5 times as large as the acoustic impedance of an object of ultrasonic inspection and a uniformly thick outer layer of a second material of which acoustic impedance is 1.6 to 2.7 times as large as the acoustic impedance of the aforementioned object and is placed on the row of the transducer elements such that the inner layer intimately covers the front electrode films of all the transducer elements.

The width-to-thickness ratio of the piezoelectric plate preferably ranges from 0.4 to 0.7.

Either lead titanate ceramic or a ceramic system composed of lead titanate, lead zirconate and lead magnesium niobate is preferred as the material of the piezoelectric plate.

As a probe for ultrasonic diagnostic equipments, it is preferable to use arsenic sulfide glass, crown glass or fused quartz as the material of the inner layer of the acoustic impedance matching layer and a synthetic resin for the outer layer.

The probe does not need to be provided with any backing load layer, so that the back electrode films are preferably exposed to the atmosphere. It is preferable that no substance other than air is present in the intervals between the transducer elements.

The invention will fully be understood from the following detailed description with reference to the accompanying drawings, wherein.

FIFG. 11 shows the shape and arrangement of the transducer elements in the same probe.

As the fundamental material of an ultrasonic transducer, a wide use has been made of piezoelectric ceramic materials other than piezoelectric crystalline materials such as quartz crystal and lithium niobate. Examples of currently used ceramic materials are lead titanate (will hereinafter be referred to as PC-1), twocomponent piezoelectric ceramics such as lead titanate zirconate (referred to as PC-2) and three-componentpiezoelectric ceramics such as a system (referred to as PC-3) composed of lead titanate, lead zirconate and lead magnesium niobate.

A phenomenon that WL vibration modes interfere with TL vibration of a rectangular plate of a piezoelectric material while the width-to-thickness ratio(W/t) of the plate takes rather small values is observed in different manners for different types of materials. This is because of differences in electromechanical coupling coefficients among the ceramic materials. Relative intensities of TL vibration and WL vibration for each material can be estimated from the electromechanical coupling coefficients of the material regarding the respective modes of bibrations The electromechanical coupling coefficients $k_t$ and $k_{33}$ of a piezoelectric ceramic material respectively regarding TL vibration and WL vibration are given by the following equations.

$$k_t = e_{33} \sqrt{\frac{\epsilon_{33}^S}{c_{33}^D}}$$

-continued $$k'_{31} = \frac{k_{31}}{\sqrt{1-(k_{31})^2}} \sqrt{\frac{1+\sigma^E}{1-\sigma^E}}$$

where $$k_{31} = \frac{d_{31}}{\sqrt{\epsilon_{33}^T \cdot s_{11}^E}}$$

$e_{33}$: piezoelectric stress constant of the ceramic material
$\epsilon_{33}^S$: dielectric constant of the ceramic material under fixed strain
$c_{33}^D$: modulus of elasticity of the ceramic material
$d_{31}$: piezoelectric modulus of the ceramic material
$\epsilon_{33}^T$: dielectric constant of the ceramic material under fixed stress
$s_{11}^E$: compliance constant of the ceramic material
$\delta^E$: Poisson's ratio of the ceramic material To produce an ultrasonic transducer which operates in TL vibration mode, a piezoelectric material for the transducer is desired to have a large value for the coefficient $k_t$ and a small value for $k'_{31}$. Table 1 shows examples of the three kinds of ceramic materials PC-1, PC-2 amd PC-3.

Table 1

| Material | Electromechanical coupling coefficients | | | Resonance frequency constants (MHz mm) | | $\epsilon^S$ |
|---|---|---|---|---|---|---|
| | Thickness longit. vibration $k_t$ | Width longit. vibration $k'_{31}$ | Width expansion vibration $k'_{33}$ | Thickness longit. vibration $N_t$ | Width expansion vibration $N'_{33}$ | |
| PC-2 | 0.49 | 0.53 | 0.66 | 1.9 | 1.4 | 830 |
| PC-3 | 0.46 | 0.54 | 0.66 | 1.9 | 1.4 | 770 |
| PC-1 | 0.48 | 0.07 | 0.71 | 1.1 | 1.4 | 140 |

(Values for the electromechanical coupling coefficients of other two-component and three-component ceramic materials do not significantly differ from the values for PC-2 and PC-3 presented in Table 1.)

Both PC-2 and PC-3(and a differently composed twomaterials) have considerably large values for $k'_{31}$ as can be seen in Table 1. Accordingly the interference of WL vibration modes with TL vibration occurs when an ultrasonic transducer based on one of these ceramic materials has the shape of an elongate rectangular plate without any particular consideration of the ratio W/t of the plate. For ultrasonic transducer using PC-1 which is characterized by a very small value for $k'_{31}$, (W/WL vibration modes have a far less influence on TL vibration.

Figure 4:
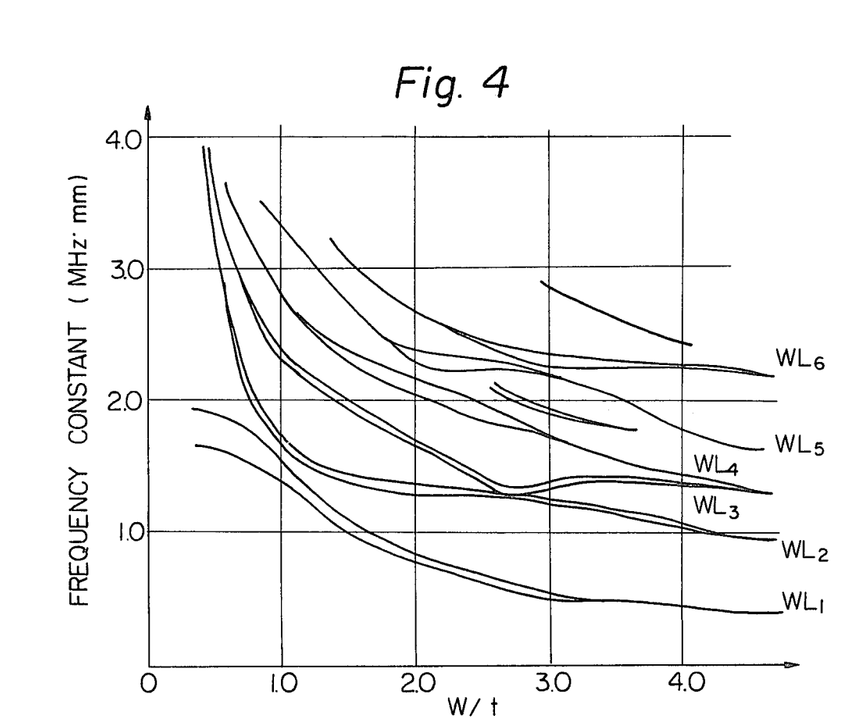
FIG. 4 is a graph showing variations in resonant and antiresonant frequency constants of a rectangular plate of a piezoelectric ceramic material with a variation in the width-to-thickness ratio of the plate.

We have performed exhaustive experimental works to thoroughly examine the influence of WL vibrations on TL vibration for currently available piezoelectric ceramic materials. FIG. 4 shows the relationship between W/t of a rectangular plate of an example of PC-3 and its frequency constant (f·t) regarding WL vibration modes, obtained by our experiments. In each of the paired curves such as WL$_1$, WL$_2$, . . . . . , WL$_6$, the lower curve represents resonance frequency constant and the upper curve antiresonance frequency constant. While the value for the ratio W/t is sufficiently large (w/t > about 5), the frequency constant f·t regarding TL vibration does not depend on W/t but remains constant (about 2 MHz·mm). There arises an influence of WL vibrations on TL vibration when W/t is decreased below about 5. Then the frequency constant regarding TL vibration no longer remains constant but tends to gradually increase as the ratio W/t is decreased. Particularly when W/t is between about 3 and 2, a curve representing the relationship between W/t and f·t. regarding TL vibration (if such a curve were drawn in FIG. 4) cannot be distinguished from the curves representing wL vibrations. When W/t is around 2.5, the plate vibrates in a complicated mode because of the coupling of TL vibration with both WL$_4$ and WL$_5$.

When TL vibration is coupled with WL vibrations, the rectangular plate or transducer element can no longer make a simple piston movement in the direction of its thickness. It is a fundamental condition of success in obtaining a good ultrasonic signal from an ultrasonic probe subjected to electronic scanning that each transducer element of the probe functions as a simple piston sound source, but this condition cannot be met if occurs the above described coupling of different vibration modes.

Evil effect produced by coupling of vibration modes is typically materialized as a distortion in the ultra sound radiation pattern of the probe as is demonstrated by the following experimental result and theoretical analysis.

Figure 5:
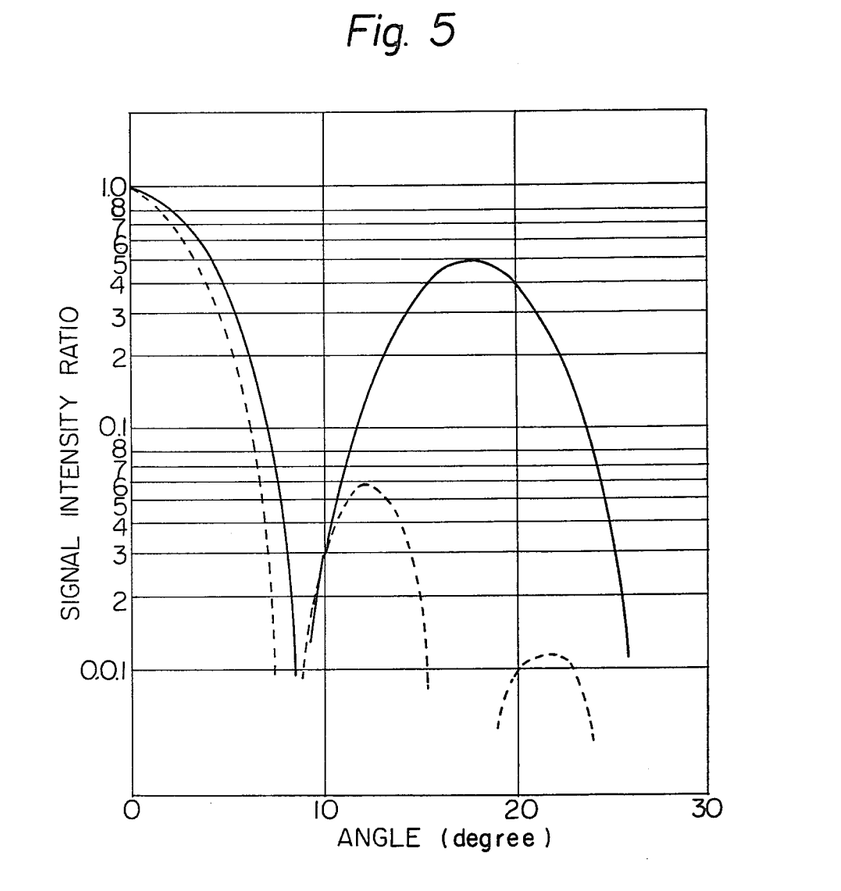
FIG. 5 shows a radiation pattern of an ultrasonic probe which is not in accordance with the invention.
Figure 6:
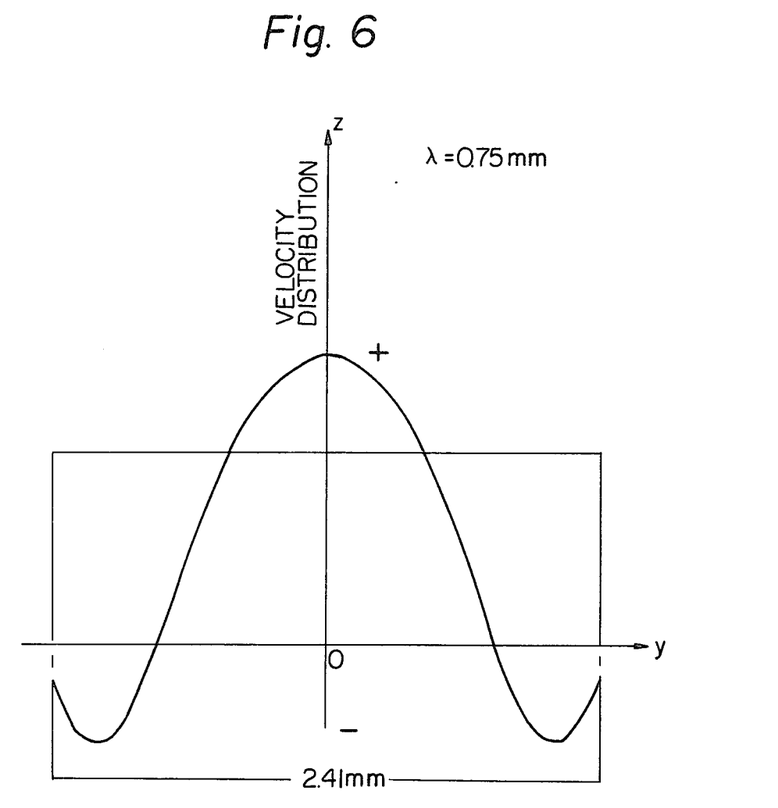
FIG. 6 is an example of particle velocity distribution on the same probe.

In FIG. 5, the curve in solid line is an experimentally obtained far field radiation pattern of an ultrasonic probe which had two transducer elements of PC-3 in the shape of a rectangular plate with a W/t ratio of 2.5. The curve in broken line represents a theoretical pattern on the assumption that the probe functioned as a piston sound source. Reckoning from FIG. 5, the velocity distribution on the surface of the tested transducer elements was judged significantly distored. Such distortion is caused by the coupling of the TL vibration of the elements with WL$_4$ and WL$_5$ vibrations shown in FIG. 4. FIG. 6 shows an example of the distribution in the y-direction of the ultrasonic vibration velocity in the z-direction on the surface of a PC-3 element. in FIG. 7, the curve in solid line shows a far field radiation pattern obtained when a transducer element exhibiting a velocity distribution as shown in FIG. 6, and the curve in broken line shows a far field radiation pattern of a piston sound source. As demonstrated by the radiation patterns of FIG. 5, a coupling of different vibration modes caused a distortion of the radiation pattern, particularly great enlargement of side lobes. When ultrasonic inspection is performed with such distortion in the radiation pattern of the transducer elements, ultrasonic signal received in the inspection and, hence, pictures based on the received signal suffer significant deterioration in quality represented by, e.g., intensity, resolution and contrast ratio.

Figure 7:
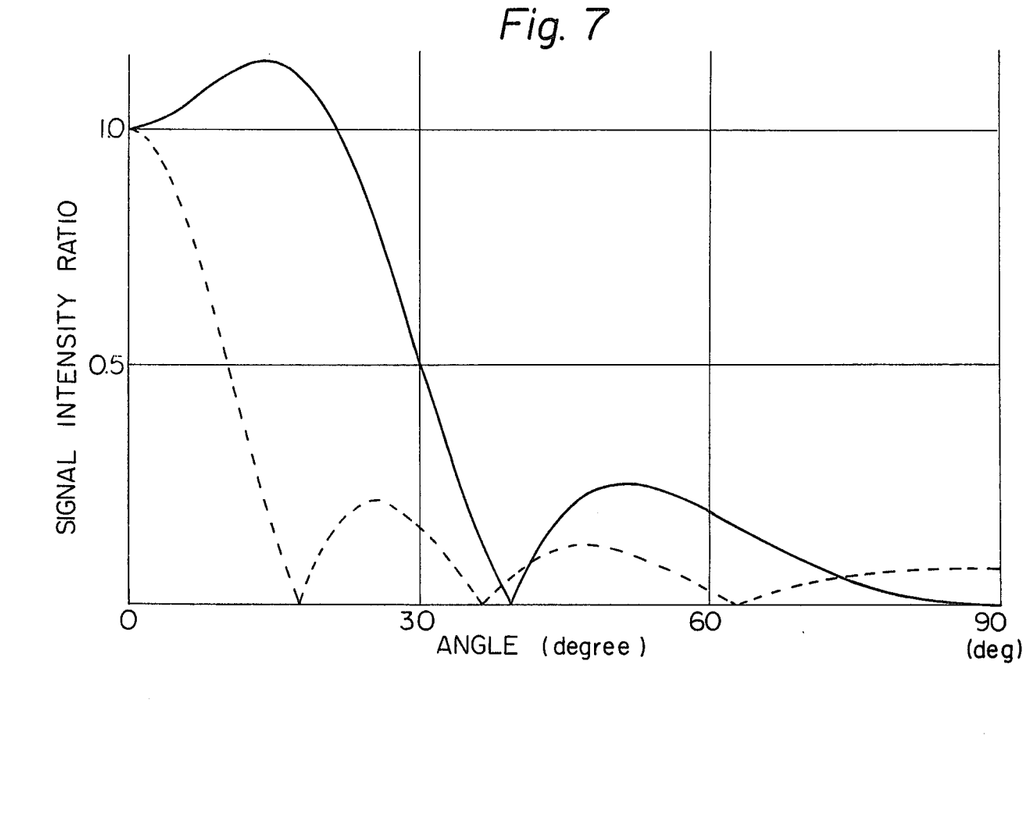
FIG. 7 shows an ultrasound radiation pattern based on the data of FIG. 6.

A distorted radiation pattern as illustrated in FIGs. 5-7 is not specific to PC-3. Our experiments were carried out on various kinds of currently available piezoelectric ceramic materials to confirm that all the ceramic materials except PC-1 gave unsatisfactory signals or pictures as the result of a coupling of TL and WL vibration modes.

The experimental result presented in FIG. 5 was obtained by immersing the transducer elements in water without the provision of any impedance matching layer and measuring the intensity of ultrasonic signal reflected from an underwater target. The distortion in the ultrasound radiation pattern was considerably diminished by applying an acoustic impedance matching layer of a particular structure, which will later be described.

In an ultrasonic probe according to the invention, the transducer elements do not particularly differ from the elements in conventional probes in their material, fundamental shape and arrangement. However, it is one of important features of the invention that the W/t ratio of each element (more accurately the plate of a piezoelectric material) takes a value not greater than 0.8, and preferably between 0.4 and 0.7. We have discovered that the above described coupling of TL and WL vibration modes can fundamentally be avoided by the employment of such a value for W/t of the rectangular plate as the essential part of the transducer element. The basis of the specified value for W/t is as follows.

Figure 8:
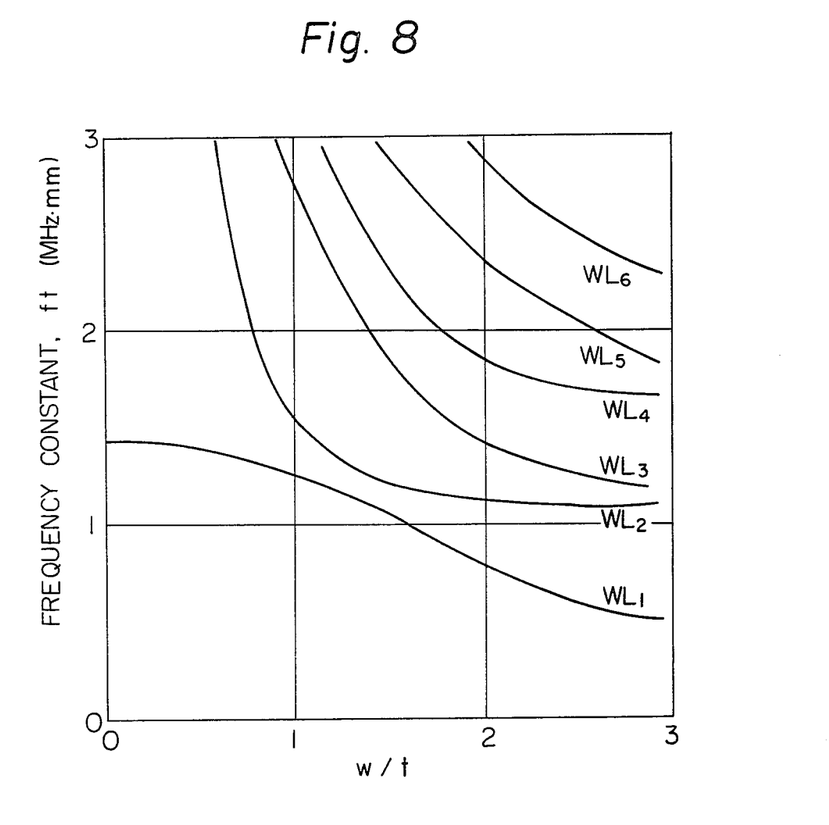
FIG. 8 is a graph showing theoretical variations in resonant frequency constant of a rectangular plate of a piezoelectric ceramic material with a variation in the width-to-thickness ratio of the plate.

FIG. 8 shows substantially the same matter as FIG. 4, but the curves of FIG. 8 are theoretical ones obtained on PC-3 by calculations which were an expansion of fundamental methods presented by R. Holland, "Journal of Acoustical Society of America", Vol. 46, 989 (1974) and D. C. Gazis et al, "Journal of Applied Mechanics", Sept., 1960, p. 541. Analysis by "Finite Element" method also gives these curves. On ultrasonic probes it is a common practice to utilize either short pulses or a tone-burst signal for exciting the transducer elements with the purpose of augmenting the longitudinal resolution. Then an ultrasonic probe receives a reflected signal which results from intensity modulation of a transmitted pulse signal, so that the received signal has a certain bandwidth with the center frequency $f_o$ of the transmitted signal as the center. In general, the bandwidth $\Delta f$ can be taken as: $\Delta f \simeq f_o/2$ The application of an ultrasonic signal having such a broad bandwidth inevitably results in the excitation of several different vibration modes. Referring to FIG. 8, when the PC-3 element has a W/t ratio of 2 by way of example and is operated fundamentally in TL vibration mode of which frequency constant is about 2 MHz·mm, there occurs a simultaneous excitation of WL vibrations such as $WL_3$, $WL_4$ and $WL_5$ of which frequency constants $f \cdot t$ at this W/t stand within an 1 MHz·mm wide range extending on both sides of the frequency constant of the TL vibration, about 2 MHz·mm. The thus caused WL vibrations interfere with the TL vibration and unfavorably influence the characteristic of the element in a manner as described hereinbefore.

In the present invention, W/t of the transducer element is made very small with the intention of positively utilizing the lowermist WL vibration mode, $WL_1$, in FIG. 8. As can be seen in FIG. 8, the respective frequency constants of higher WL vibration modes exhibit great increase as W/t of the element is decreased, but the frequency constant of $WL_1$ mode exhibits only a moderate increase. Consequently, a great difference arises between a frequency at which occurs $WL_1$ vibration and a higher frequency at which occurs $WL_2$ vibration (or a still higher mode) if W/t takes a sufficiently small value. When W/t is 0.08, the gap between $WL_1$ mode and $WL_2$ mode amounts to 0.7 MHz·mm. In other words, the ratio $\Delta f/f_o$ regarding these two modes takes a value of about 1, i.e., a value distinctly larger than ½, at this W/t. If $WL_1$ mode is utilized as a fundamental vibration mode, therefore, no unwanted vibration mode exists within the bandwidth of a ultrasonic signal obtained by the fundamental vibration so long as W/t of the element is 0.8 or smaller. From this reason, a transducer element of the described shape with a W/t ratio of not greater than 0.8 exhibits a sound wave radiation pattern which is very close to the radiation pattern of a piston sound source. Accordingly, theoretically established techniques for particular purposes such as suppression of side lobes and accomplishment of phase control can surely be applied to such a transducer element.

When W/t of a rectangular plate is sufficiently small, the vibration of the plate in $Wl_1$ mode occurs as width extensional vibration of plate in marked contrast to thickness vibration of plate commonly utilized in ultrasonic probes for inspection equipments of the electronic scanning type. Both the frequency constant and electromechanical coupling coefficient of piezoelectric materials take different values with respect to different vibration modes. For the typical piezoelectric ceramics PC-1, PC-2 and PC-3, the frequency constant $N'_{33}$ and the electromechanical coupling coefficient $k'_{33}$ both regarding width extensional vibration of plate are also presented in Table 1. It is particularly worthy of notice in Table 1 that the values for $k'_{33}$, which deserves consideration when the materials are shaped to have sufficiently small W/t, are considerably greater than the values for $k_t$. As is well known an ultrasonic probe exhibits better characteristic as the electromechanical coupling coefficient takes a larger value. Since vibraton of the transducer elements in a probe according to the invention can be regarded substantially as width extensional vibration of plate, it comes out that the elements have a considerably larger value for the electromechanical coupling coefficient than the value in the case of making thickness longitudinal vibration as is usual in conventional probes. Accordingly an ultrasonic probe of the invention exhibits a greatly improved characteristic.

Figure 9:
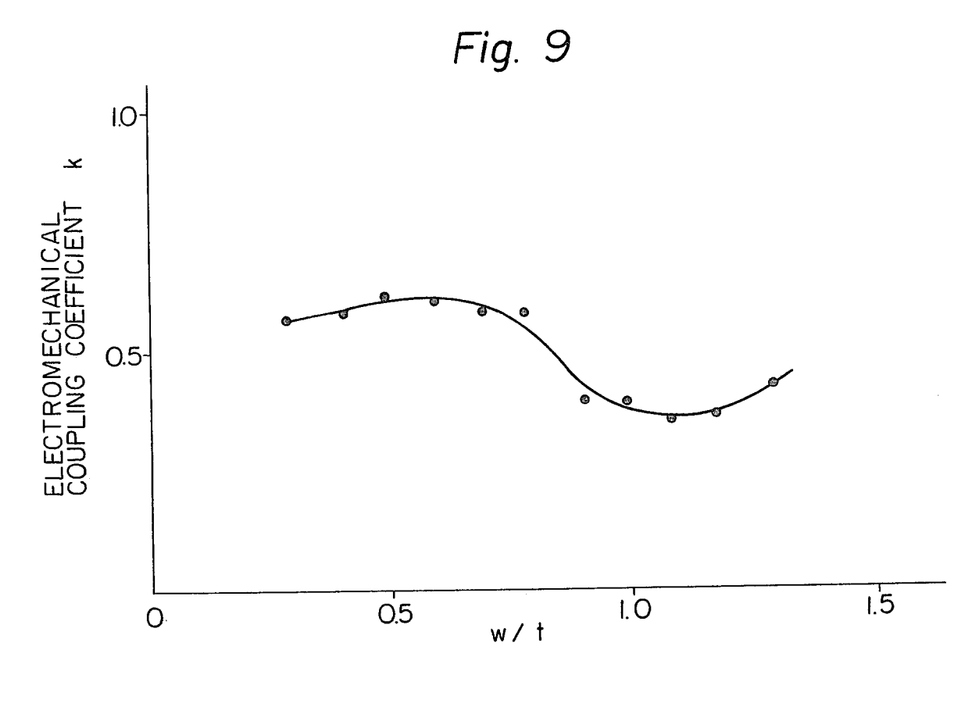
FIG. 9 is a graph showing the dependence of an electromechanical coupling coefficient of a rectangular plate of a piezoelectric ceramic material on the widthto-thickness ratio of the plate.

The symbol $k'_{33}$ represents an effective electromechanical coupling coefficient which has meaning when W/t is sufficiently small. It is possible to experimentally determine the value of effective electromechanical coupling coefficient $k$ at any W/t which may not sufficiently be small. FIG. 9 shows an experimentally determined relationship between W/t and the effective electromechanical coupling coefficient $k$ for a rectangular plate of PC-3. It is clearly shown that $k$ takes a considerably large value when W/t is below 0.8 and maximizes while W/t stands between 0.4 and 0.7.

Figure 10:
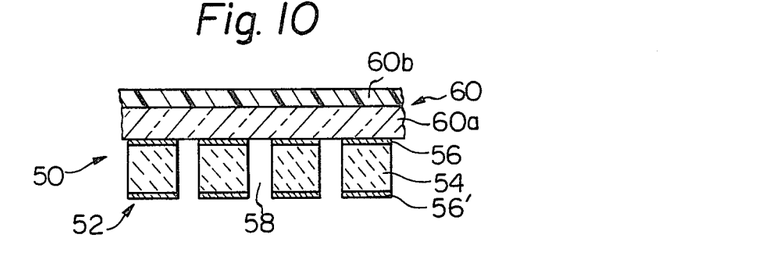
FIG. 10 is a fragmentary, sectional and elevational view of an ultrasonic probe according to the invention.

FIG. 10 shows a fundamental construction of an ultrasonic probe 50 according to the invention. Similarly to the conventional ultrasonic probe 10 of FIG. 1, this probe 50 has a multiplicity of transducer elements 52 which have the shape of a rectangular plate and are arranged in a row at small intervals. Each element 52 is an elongate rectangular plate 54 of a piezoelectric material with two electrode films 56 and 56' respectively coated on its front and back surfaces. Piezoelectric ceramics including lead titanate (PC-1), two-component systems such as lead titanate zirconate (PC-2) and three-component systems typified by a system composed of a lead titanate, lead zirconate and lead magnesium niobate (PC-3) are useful as the material of the plate 54. The use of lead titanate or PC-3, particularly the latter, is most preferred. However, the use of a crystalline material such as quartz crystal or $LiNbO_3$ is also permissible. A selected piezoelectric material is shaped into the plate 54 such that the direction of the thickness $t$ of the plate 14 coincides with the direction of polization when the material is a ceramic material but does with the direction of c-axis in the case of a crystalline material. The piezoelectric plate 54 must have a definite width-to-thickness ratio which is not greater than 0.8 and preferably between 0.4 and 0.7. The electrode films 56, 56' utilize a commonly employed metal such as Ag, Al, Au, Cu or In as their material and are formed by vacuum evaporation, soldering, plating, flame spraying or application of a paint followed by baking.

Figure 11:
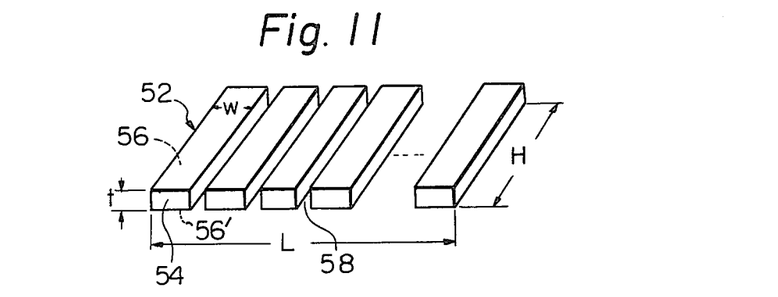

The rectangular elements 52 are arranged in a row, for example in a straight linear row, with their longer sides (normal to the surfaces coated with the electrode films 56,56') opposite to each other as shown in FIG. 11. It is necessary to arrange the elements 52 at intervals since any acoustic coupling of two adjacent elements 52 can be avoided by the presence of gaps 58 between the elements 52. The presence of any solid substance in these gaps 58 must strictly be avoided because there occurs interference between the adjacent elements, causing cross talk of the signals, if even a small volume of solid substance is present in any of the gaps 58. In practical applications, therefore, the gaps 58 are filled with air or may alternatively be evacuated. It is desirable that the width of the gaps 58 be as small as possible: the lower limit is determined by manufacturing technique.

Figure 12:
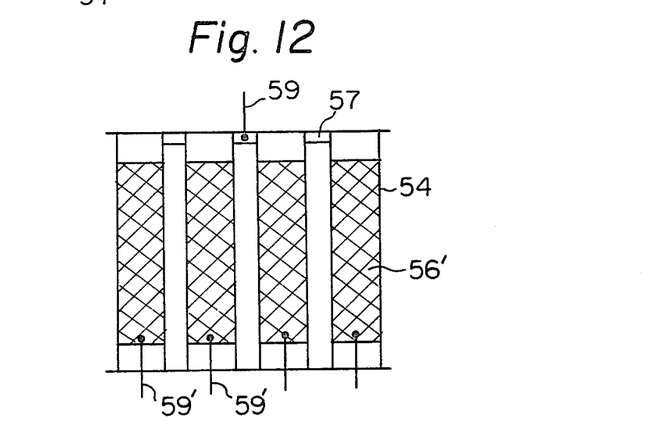
FIG. 12 is a rear plan view of the same probe.

FIG. 12 is a rear plan view of the row of the elements 52. The front electrode films 56 of the respective elements 52 are connected together by interelectrode connectors 57 so as to serve as a common electrode, and a lead 59 is provided for these electrode films 56. The back electrode films 56' are individually provided with leads 59'.

Referring again to FIG. 10, the probe 50 has an acoustic impedance matching layer 60 which is placed on the row of the transducer elements 52 so as to in intimately contact and entirely cover the front electrode films 56 of all the elements 52. The structure of the impedance matching layer 60 is another important feature of the invention. In this probe 50, the impedance matching layer 60 consists of a uniformly thick inner layer 60a, which is in contact with the electrode films 56, and a uniformly thick outer layer 60b which is bonded to the outside of the inner layer 60a over the entire area. Accordingly, the outside of the outer layer 60b is brought into contact with an object of ultrasonic inspection or diagnosis. The inner and outer layers 60a and 60b are different in material as will hereinafter be described. A fully practicable probe can be obtained even when an acoustic impedance matching layer is formed as a single layer of an appropriate material, but the employment of a double-layer or laminated structure for the impedance matching layer, in combination with the above described transducer elements 52, is distinctly advantageous.

The structure of the acoustic impedance matching layer 60 was determined with full consideration of two indices, namely, insertion gain (I.G.) and differential phase (DP), which are known as appropriate for the evaluation of the characteristic of the probe 50. I.G. is an indication of electrical-mechanical conversion efficiency: the greater the value for I.G, the better the efficiency. DP has connection with the magnitude of temporal distortion of a signal subject to conversion by a transducer. Less distortion of the signal occurs as DP exhibits less variation with respect to frequency. Detailed explanation on I.G and DP is given, for example, by K. E. Sittig, "TEEE Transactions on Sonics and Ultrasonics", Vol. 14, No. 4, 167 (1967). Our experimental researches concerning I.G and the frequency dependence of DP for various materials have revealed the preferableness of selecting the materials for the inner and outer layers 60a and 60b of the acoustic impedance matching layer 60 on the following principle.

A material of which acoustic impedance is 2.5 to 9.5 times as large as the acoustic impedance of an object of inspection using the probe 50 is chosen for the inner layer 60a. The material for the outer layer 60b is required to have an acoustic impedance smaller than the material for the inner layer 60a but 1.6 to 2.7 times the acoustic impedance of the aforementioned object.

When the probe 50 is for use in ultrasonic diagnostic equipments (the object is human body), arsenic sulfide glass is most preferable as the material of the inner layer 60a, and crown glass comes next, and then fused quartz. Flint glass, heavy flint glass and germanium sulfide glass are also useful as the material of the inner layer 60a. On the other hand, various synthetic resins such as epoxy resin, acryl resin, polystyrene, PVC,ABS resin, and cyno resin are useful for the outer layer 60b, and the use of epoxy resin is most preferred.

The thickness of the inner and outer layers 60a and 60b is preferably determined so as to meet the following condition. For the inner layer 60a, its thickness is made to range from 45 to 68% of a value given by $V_a/2f$) where $V_a$ is the sound velocity in the material of the inner layer 60a and $f$ is the frequency of the ultrasonic wave, while the thickness of the outer layer 60b ranges from 48 to 64% of a value given by $(V_b/2f)$ where $V_b$ is the sound velocity in the material of the outer layer 60b.

When the respective layers 60a and 60b of the impedance matching layer 60 have such thicknesses, the thickness of the piezoelectric plates 54 is preferably determined such that the thickness $t$ ranges from 80 to 120% of a value given by $(N'_{33}/f)$.

Although not preferred in this invention, it is possible to form an acoustic impedance matching layer as a single layer for a probe utilizing the transducer elements 52 according to the invention. In this case, the impedance matching layer is made of a material of which acoustic impedance is 2 to 4 times as large as the acoustic impedance of an object of inspection. The use of crown glass or germanium sulfide glass is preferable.

The probe 50 does not need the provision of any backing load (20 in FIG. 1), so that the back side electrode films 56' are usually exposed to the atmosphere. However, it is permissible that the probe 50 includes a backing load layer made of a material of which acoustic impedance is smaller than that of an object of inspection. Wax or light plastics serves as such material.

A probe according to the invention has the advantage that the transducer elements 52 can vibrate almost as a piston without influenced by unwanted vibration modes. Theoretical analysis of the vibration of the elements 52 was performed by a technique called "Finite Element Method" or "Matrix Method". As can be seen in many textbooks, stress, strain and displacement are calculated by this method for each small portion of a body from input data such as load conditions, properties of the material and the structure of the body.

Figure 13:
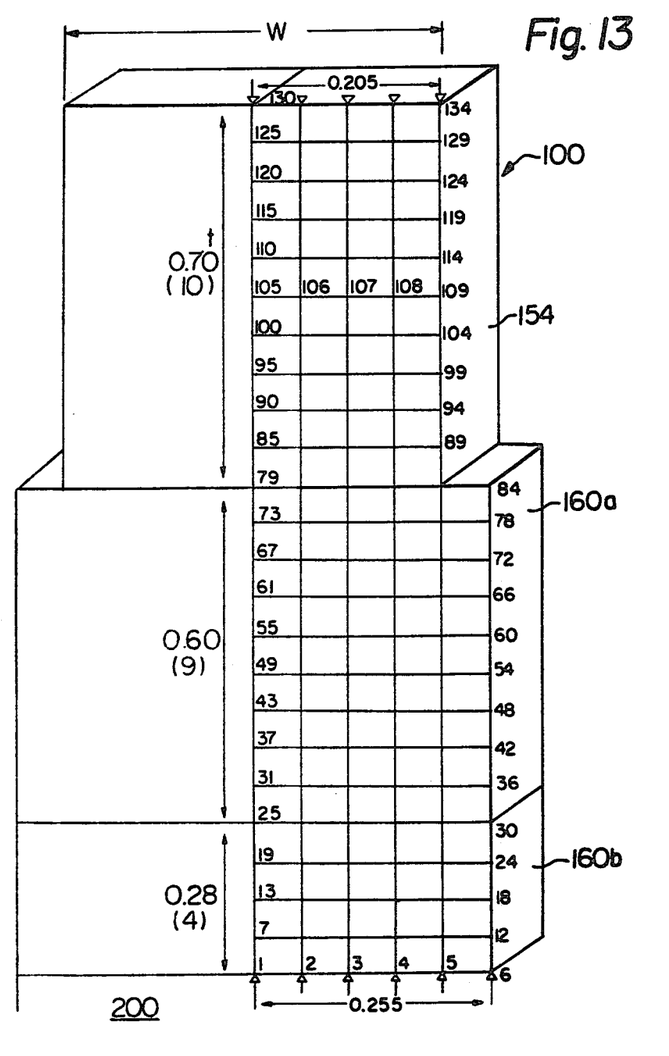
FIGs. 13–16 are models of a probe according to the invention, showing vibration modes of the probe as the result of analysis by finite element method.

Referring to FIG. 13, the analysis was carried out on a model 100 which was made up of a rectangular plate 154 of PC-3, a plate 160a of fused quartz and a plate 160b of epoxy resin. The piezoelectric plate 154 was 0.7 mm in thickness ($t$), 0.41 mm in width (W) and 10 mm in length (H). The fused quartz plate 160a and the epoxy resin plate 160b (which serves as the inner and outer layers 60a and 60b of the acoustic impedance matching layer 60 in FIG. 10.) were commonly indefinite in width and 10 mm in length. The fused quartz plate 160a was 0.6 mm thick, while the epoxy plate 16:b was 0.28 mm thick. These values for the thickness of the respective plates 154, 160a and 160b satisfied the above described conditions. Reference numeral 200 indicates a medium or load in which the vibration is transmitted. In this analysis, the medium 200 was assumed to be water.

Figure 14:
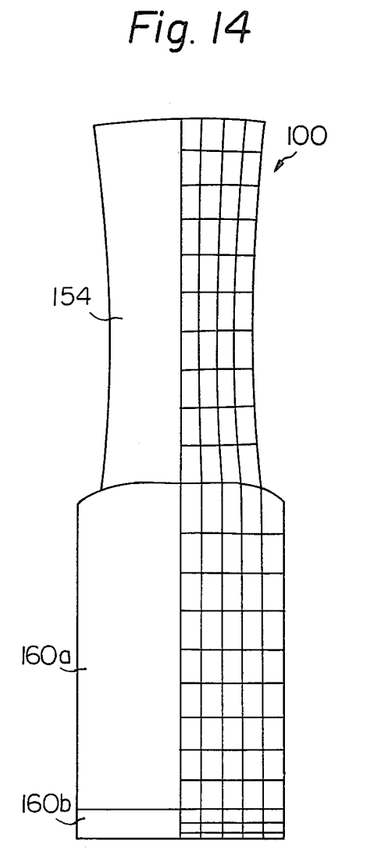
Figure 15:
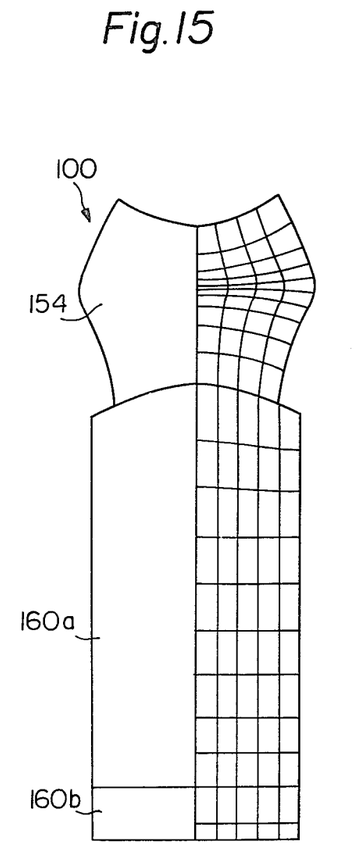
Figure 16:
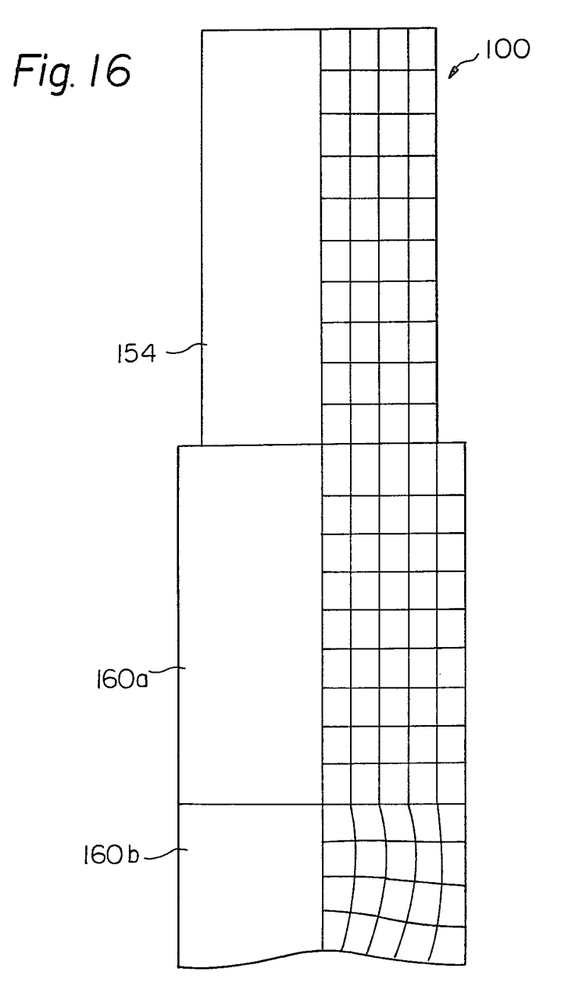

As the result of the analysis, FIG. 14 shows a displacement distribution on the model of FIG. 13 when the piezoelectric plate 154 vibrated in a fundamental mode corresponding to $WL_1$ mode in FIG. 8. It was theoretically confirmed by FIG. 14 that the elements 52 in the probe 50 accordance to the invention make an almost ideal piston vibration in their fundamental mode. FIGS. 15 and 16 show the manners of vibration of the same model 100 in higher modes also as the result of the analysis. FIG. 16 demonstrates that the actual vibration exhibits a deviation from piston vibration in higher modes. However, as can be understood from FIG. 8, resonance frequency for this plate 154 of PC-3 is as high as 4.5 MHz and sufficiently far from the frequency of the fundamental mode, 2.25 MHz. Accordingly this resonance mode has no unfavorable influence on the fundamental vibration mode.

By similar analysis on probes 50, it was confirmed that the elements 52 in the probe 50 make a piston movement when vibrated in the fundamental mode corresponding to $WL_1$ mode even when the dimensions and materials are made to variously differ (insofar as the hereinbefore described requirements are met) from those which are employed in the model 100.

Figure 17:
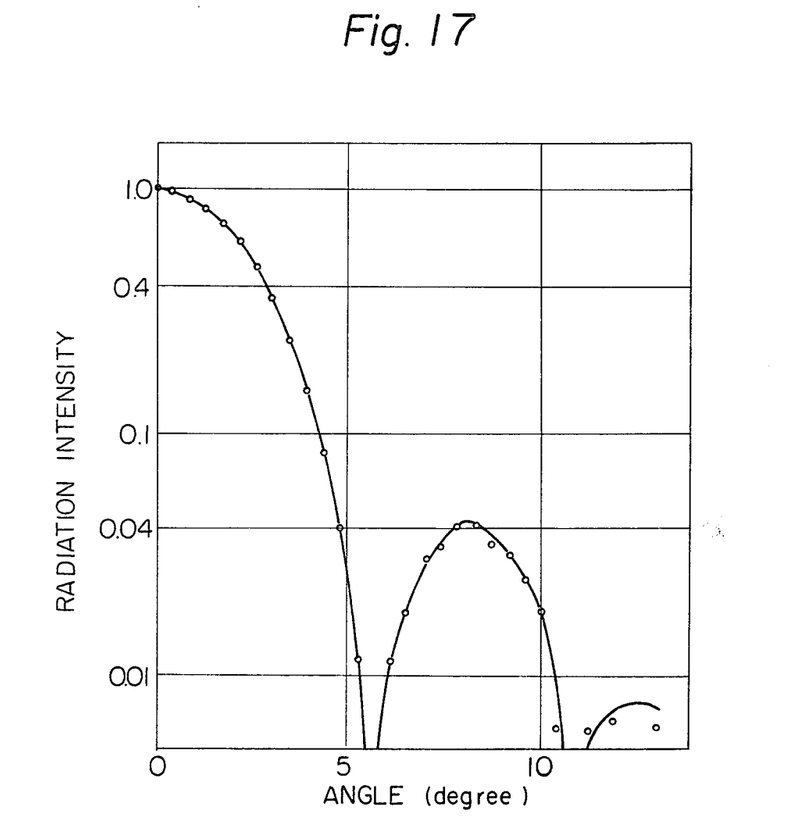
FIG. 17 shows a radiation pattern of a probe according to the invention.

FIG. 17 shows an angular distribution of the sound wave radiation intensity obtained by experiment on the probe 50 of FIG. 10 with substantially the same materials and thickness values as in the model 100 of FIG. 13. The circles in this graph represent experimental data obtained in far field, and the curve represents a theoretical pattern. A good agreement of the experimental data with theoretical values is apparent.

As will have been understood from the foregoing description, an ultrasonic probe according to the invention can operate as an almost ideal piston sound source and, hence, has the following advantages.

There arises no coupling of a fundamental vibration with unintended vibration modes. Accordingly, a remarkable simplification is realized not only in the mechanical characteristic but also in the electrical characteristic of the transducer elements or the probe, meaning ease in designing the driving circuit of the inspection equipments and lowering in the probability of electrical interference appearing between fundamental and unwanted vibration modes.

Improved insertion gain and bandwidth can be attained because of the utilization of width extensional vibration instead of commonly utilized thickness longitudinal vibration, meaning the increase in the electromechanical coupling coefficient of ceramic transducer materials from $k_t$ to $k'_{33}$.

From the same reason, a considerable decrease in the value for the acoustic impedance Zs of the transducer can be attained. For example, this value for PC-3 decreases from $36.5 \times 10^5$ (cgs) in the case of TL vibration to $25 \times 10^5$ (cgs) in the case of width extensional vibration. As a result, acoustical matching can more readily be achieved.

Owing to the realization of an almost ideal piston sound source, the control of the transmitted sound wave (e.g., weighted drive, focusing of the beams or inclined radiation) through the phase or intensity control on the drive signals to the individual transducer elements can readily and precisely be accomplished.

A probe according to the invention is particularly suitable for use in ultrasonic diagnostic equipments of the electronic scanning type but is useful also for other types of ultrasonic inspection or diagnostic equipments.

What is claimed is:

1. An ultrasonic probe for ultrasonic inspection equipments, comprising:
    a plurality of transducer elements, each being a rectangular plate of a piezoelectric material with front and back electrode films respectively coated on front and back surfaces thereof, said plate having a width-to-thickness ratio of not greater than 0.8, said transducer elements being arranged in a row at intervals with their longer sides opposite to each other so that said plate can make a width extensional vibration as a fundamental vibration mode; and
    an acoustic impedance matching layer, consisting of a uniformly thick inner layer of a first material placed on said row of said transducer elements to intimately cover said front electrode films of all the transducer elements and a uniformly thick outer layer of a second material placed on said inner layer to intimately cover the outer surface of said inner layer,
    the acoustic impedance of said first material being 2.5 to 9.5 times as large as the acoustic impedance of an object of ultrasonic inspection, the acoustic impedance of said second material being smaller than the acoustic impedance of said first material but is 1.6 to 2.7 times as large as the acoustic impedance of said object.

2. An ultrasonic probe as claimed in claim 1, wherein said width-to-thickness ratio is in the range from 0.4 to 0.7.

3. An ultrasonic probe as claimed in claim 2, wherein said piezoelectric material is lead titanate ceramic.

4. An ultrasonic probe as claimed in claim 2, wherein said piezoelectric material is a ceramic system composed of lead titanate, lead zirconate and lead magnesium niobate.

5. An ultrasonic probe as claimed in claim 2, wherein said first material is a glass selected from the group consisting of arsenic sulfide glass, crown glass, fused quartz, germanium sulfide glass, flint glass and heavy fling glass, said second material being a synthetic resin selected from the group consisting of epoxy resin, polystyrene, acryronitrile-butadiene-styrene resin, polyvinyl chloride, acryl resin and cyano resin.

6. An ultrasonic probe as claimed in claim 2, wherein said first material is a glass selected from the group consisting of arsenic sulfide glass, crown glass and fused quartz, said second material being epoxy resin.

7. An ultrasonic probe as claimed in claim 6, wherein said inner layer has a thickness ranging from 45 to 68% of a value given by ($V_a/2f$) said second layer having a thickness ranging from 48 to 64% of a value given by ($v_b/2f$) where $f$ is the frequency of an ultrasonic wave to be produced by the probe, $V_a$ is sound velocity in said first material and $V_b$ is sound velocity in said second material.

8. An ultrasonic probe as claimed in claim 2, wherein only air is present in gaps between said transducer elements.

9. An ultrasonic probe as claimed in claim 8, wherein said back electrode films of all the transducer elements are entirely exposed to the atmosphere.

10. An ultrasonic probe as claimed in claim 8, further comprising a backing load layer which is made of a material having an acoustic impedance smaller than the acoustic impedance of said object and placed on said row of said transducer elements to cover said back electrode films of all the transducer elements.

11. An ultrasonic probe for ultrasonic inspection equipments, comprising:

a plurality of transducer elements, each being a rectangular plate of a piezoelectric ceramic material with front and back electrode films respectively coated on front and back surfaces thereof, said plate having a width-to-thickness ratio of not greater than 0.8, said transducer elements being arranged in a row at intervals with their longer sides opposite to each other so that said plate can make a width extension vibration as a fundamental vibration mode; and an acoustic impedance matching layer of a uniform thickness placed on said row of said transducer elements to intimately cover said front electrode films of all the transducer elements, said impedance matching layer consisting of a material of which acoustic impedance is 2 to 4 times as large as the acoustic impedance of an object of ultrasonic inspection.

12. An ultrasonic probe as claimed in claim 11, wherein said material of said impedance matching layer is a glass selected from the group consisting of germanium sulfide glass and crown glass.

* * * * *